United States Patent [19]

Ho

[11] Patent Number: 5,705,653

[45] Date of Patent: Jan. 6, 1998

[54] PROCESS FOR THE PREPARATION OF A $\beta_3$-AGONIST

[75] Inventor: Guo J. Ho, Scotch Plains, N.J.

[73] Assignee: Merck & Co., Inc., Rahway, N.J.

[21] Appl. No.: 794,956

[22] Filed: Feb. 4, 1997

Related U.S. Application Data

[60] Provisional application No. 60/013,595, Mar. 18, 1996.

[51] Int. Cl.$^6$ .............................................. C07D 257/04
[52] U.S. Cl. ...................................................... 548/251
[58] Field of Search ............................................ 548/251

[56] References Cited

U.S. PATENT DOCUMENTS 5,541,197  7/1996  Fisher ........................................ 514/311

*Primary Examiner*—Robert W. Ramsuer
*Attorney, Agent, or Firm*—Mollie M. Yang; David L. Rose

[57] ABSTRACT

3-Cyclopentylpropylazide and p-chlorosulfonylphenylisocyanate undergo cycloaddition to form 1-cyclopropyl-4-(p-chlorosulfonylphenyl) tetrazone-5-one, a key intermediate in the synthesis of an important β3-agonist.

22 Claims, No Drawings

PROCESS FOR THE PREPARATION OF A β₃-AGONIST

CROSS REFERENCE TO RELATED APPLICATIONS

This application is based on, and claims priority from, provisional application No. 60/013,595 filed Mar. 18, 1996.

SUMMARY OF THE INVENTION

This invention is concerned with a process for the preparation of a compound of structural formula I:

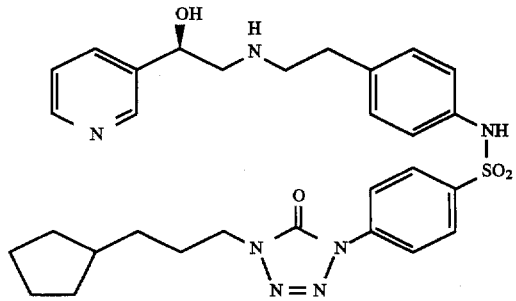

which is a β₃-agonist useful in the treatment of obesity and diabetes. A key step in the overall process for Compound I is a cycloaddition reaction to construct the tetrazonone portion of the molecule which can be illustrated as follows:

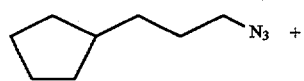

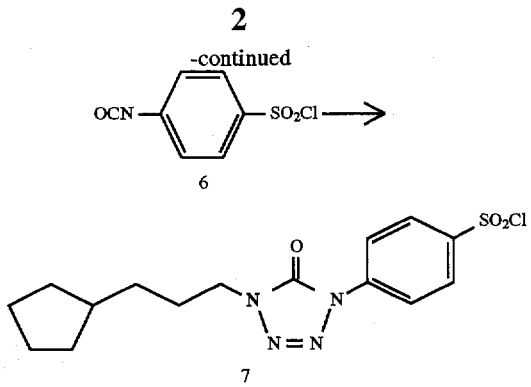

BACKGROUND OF THE INVENTION

The β₃-agonist,I, and the key intermediate,II, produced by the novel process of this invention, are known compounds being described in Patent Publication WO 95/29159. Processes for the preparation of the Compounds I and It are also disclosed in WO 95/29159. However the process to the intermediate II requires eight chemical steps from starting materials that are not readily available, and column separations, resulting in an overall yield of only 17%.

Now with the present invention, there is provided a process for the preparation of intermediate 7 which can be converted, to the final product,I, the β₃-agonist.

DETAILED DESCRIPTION OF THE INVENTION

The novel process of this invention for the preparation of Compound 7 can be depicted as follows:

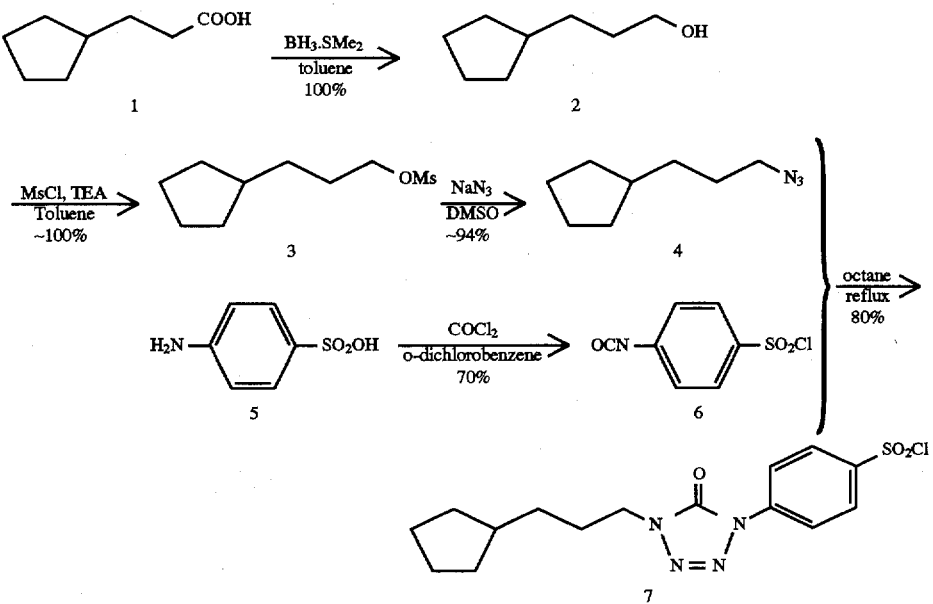

Step 1

Although cyclopentylpropanol,2, can be purchased in research quantities it is not available in bulk quantity. Therefore, it is prepared by reduction of cyclopentylpropionic acid with borane methyl sulfide complex in toluene at about 30° to 50° C. The solution is flushed with methanol after the reaction to remove the boron by-products. The unreacted acid is removed by an aqueous base wash. The yield is nearly quantitative. Alternative reducing agents are borane tetrahydrofuran complex or lithium aluminum hydride.

Step 2

The toluene solution of the alcohol from step 1 is used directly for mesylation with mesyl chloride using a strong organic base such as triethylamine as at about −10° to −40° C. The yield again is near quantitative. Although a weaker base can be used, e.g., pyridine, the excess mesyl chloride is not easily decomposed and may be carded through to the next step. Other bases that can be used are pyridine or diisopropyl ethylamine with inorganic bases such as $Na_2CO_3$, or $K_2CO_3$. Also benzenesulfonyl chloride, or toluenesulfonyl chloride can be used in place of the methanesulfonyl chloride.

Step 3

The reaction is carried out by reacting the sulfonylate with sodium azide in DMSO at about 30°–60° C. The reacting mixture is shock sensitive when the substrate concentration is greater than 130 g/L (0.67M of sulfonylate). Therefore, the reaction is performed in a concentration of about 100 g/L (0.51M). The product alkyl azide,4, is extracted into n-octane while keeping the concentration at less than 100 g/L (0.65M) throughout and the solution is used as-is for the cycloaddition.

The azide formation reaction also can be carried out under phase-transfer conditions using tetrabutylammonium salts as the catalyst in a mixture of n-octane/water. However, the reaction is very slow and accompanied by hydrolysis of the mesylate.

Step 4 p-Chlorosulfonylphenyl isocyanate is available but very expensive. Accordingly it is prepared following the procedure of U.S. Pat. No. 3,492,331 by reaction of sulfanilic acid with phosgene in o-dichlorobenzene at 165° C. using DMF as the catalyst. In the patent process, the product was isolated by vacuum distillation (0.1 mmHg, 110° C.). In the present process, the product is extracted with hot isooctane while the side products remain undissolved. This solution is then combined with that of the alkyl azide (step 3).

Step 5

The tetrazolinone ring is constructed by a cycloaddition reaction of the alkyl azide with the isocyanate in an inert organic solvent at about 110°–150° C. Conveniently, the combined solution of steps 3 & 4 is concentrated by distilling out the isooctane (b.p. 98° C.). The reaction is slow in refluxing n-octane (b.p. 125° C.). However, the product is easily isolated since it crystallizes upon cooling of the solution. The reaction procedes faster in refluxing chlorobenzene (b.p. 130° C.), but the product remains in solution together with some colored impurities. For safety issues, the reaction has to be run at a relatively dilute concentration (0.53M), resulting in a slow rate of reaction. In refluxing n-octane, the product is formed in 70–75% yield after 48 h and collected (~60% isolated yield). The filtrate, containing the two starting materials, can be subjected to further reflux to provide an additional 20% of product. Therefore, a combined yield of ~80% is usually obtained The sulfonyl chloride is purified by recrystallization from heptane.

EXAMPLE

Step 1. Reduction

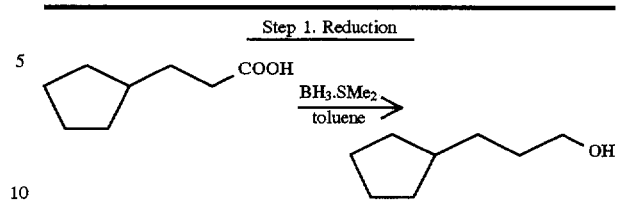

| Materials | mw | amount | mol | equiv |
|---|---|---|---|---|
| Cyclopentylpropionic acid | 142.2 | 1.2 kg | 8.44 | 1.00 |
| Borane dimethyl sulfide (d = 0.801 g/mL) | 75.97 | 705 g (880 mL) | 9.28 | 1.10 |
| Toluene | | 20 L | | |
| Bleach (5% aqueous NaOCl) | | 20 L | | |
| Methanol | | 5 L | | |
| Aqueous sodium hydroxide | 1 M | 10 L | | |
| Water | | 5 L | | |
| Product | | Theory | | |
| Cyclopentylpropanol | 128.2 | 1.08 kg | 8.44 | 1.00 |

Procedure

A 50-L reaction vessel was fitted with a thermocouple, mechanical stirrer, pressure equalizing addition funnel, nitrogen inlet, and scrubber (the scrubber was washed continuously with bleach to oxidize methyl sulfide). To the vessel was charged a solution of cyclopentylpropionic acid (1.2 kg, 8.44 mol) in toluene (12 L). A solution of borane dimethyl sulfide in toluene (2.0M, 4.65 L, 9.3 mol) was added via the addition funnel at a rate to maintain the temperature at 40°–45° C. After addition the solution was aged at 45° C. for 30 min and assayed for completion.

The reaction was quenched by (cautious) addition of methanol (2.5 L) and aged until evolution of hydrogen ceased. The solution was then concentrated by atmospheric distillation to remove ~3 L of distillate and further flushed with 2.5 L of methanol. The solution was diluted to ~13 L by addition of toluene and washed with 2×5 L of 1M aqueous sodium hydroxide, followed by 2×5 L of water. This solution was used as-is in the next step.

Assay yield: 1.09 kg (GC), ~100%.

Step 2. Mesylation

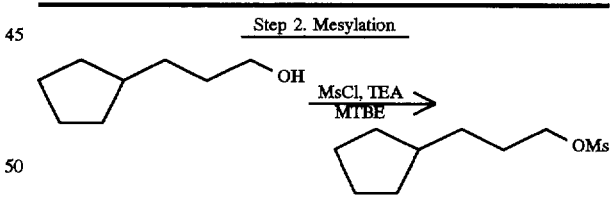

| Materials | mw | amount | mol | equiv |
|---|---|---|---|---|
| Cyclopentylpropyl alcohol (toluene solution, ~14 L) | 128.2 | 1.02 kg | 7.96 | 1.00 |
| Toluene | | ~10 L | | |
| triethylamine | 101.2 | 967 g (1.33 L) | 9.55 | 1.20 |
| Methanesulfonyl chloride | 114.6 | 1.01 kg (682 mL) | 8.76 | 1.10 |
| Aqueous HCl | 1 M | 20 L | | |
| Sat. aqueous NaCl | 20 L | | | |
| Product | | Theory | | |
| Cyclopentylpropyl mesylate | 194.2 | 1.54 kg | 7.96 | 1.00 |

Procedure

A 50-L reaction vessel was fitted with a thermocouple, mechanical stirrer, pressure equalizing addition funnel, and nitrogen inlet. A solution of cyclopentylpropyl alcohol in toluene (~14 L, 1.02 kg of the alcohol) was charged. The solution was distilled to remove water azeotropically until K.F<100 µg/mL (~1 L of distillate collected). Dry triethylamine (967 g, 9.55 mol, K.F.<100 µg/mL) was added and the solution was diluted with dry toluene to a volume of ~16 L. It was then cooled at −20—25° C. and a solution of mesyl chloride (1.01 kg, 8.76 mol) in dry toluene (5 L, K.F.<100 µg/mL) was added via the addition funnel while maintaining the temperature at <−20° C.

A white precipitate is formed during the addition of mesyl chloride. If the slurry becomes too thick, it may be diluted with toluene.

After addition of mesyl chloride the mixture was heated to 20° C. over ~1 h and aged for 2 h. The reaction was then assayed for completion.

The mixture was then cooled at 0°–5° C. and quenched by addition of 10 L of cold aqueous HCl (1M). The layers were separated and the toluene layer was washed sequentially with 10 L of cold HCl and 2×10 L of cold saturated brine. The solution was then dried over 4 Å molecular sieves for 14 h (K.F.<100 µg/mL) before used for the next step.

Assay yield: 1.54 kg, ~100%.

Step 3. Azide Formation

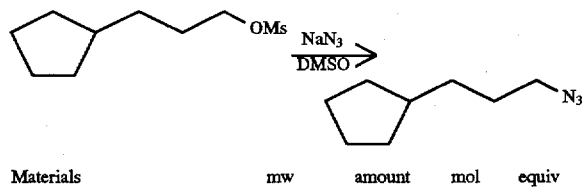

| Materials | mw | amount | mol | equiv |
|---|---|---|---|---|
| Cyclopentylpropyl mesylate (~15 L of toluene solution) | 194.2 | 1.53 kg | 7.88 | 1.00 |
| Sodium Azide | 65.01 | 566 g | 8.70 | 1.10 |
| DMSO | | 16 L | | |
| n-Octane | | 12 L | | |
| Water | | 35 L | | |
| Sodium sulfate | | 500 g | | |
| Product | | Theory | | |
| Cyclopentylpropyl azide | 153.2 | 1.21 kg | 7.88 | 1.00 |

Procedure

To a 50-L vessel fitted with a thermocouple, mechanical stirrer, and nitrogen inlet was charged a solution of cyclopentylpropyl mesylate (1.53 kg, 7.88 mol) in toluene (~15 L of solution). Toluene was removed by vacuum distillation at 50°–55° C. The resulting liquid (~1.5 L) was diluted with DMSO (16 L). To this solution was added sodium azide portionwise (566 g, 8.7 mol) at 40°–45° C. over 2 h. The resulting mixture was aged at 40°–45° C. until the reaction was assayed to be complete (~4 h).

Caution: The concentration of the starting mesylate in DMSO must be kept <100 g/L. The reaction mixture becomes shock sensitive if the concentration is >130 g/L. The reaction temperature should be maintained at >40° C. to prevent accumulation of unreacted sodium azide.

After the reaction was complete, n-octane (12 L) was added, followed by addition of 35 L of water. The phases were separated and the octane solution was washed with water (5 L) and saturated brine (5 L). The solution was then dried over sodium sulfate (~500 g) for 0.5 h and filtered. The solution was then stored at 0°–5° C.

The azide solution is very stable at 0°–5° C.

Assay yield: 1.13 kg, 93%.

Step 4. Isocyanate Formation

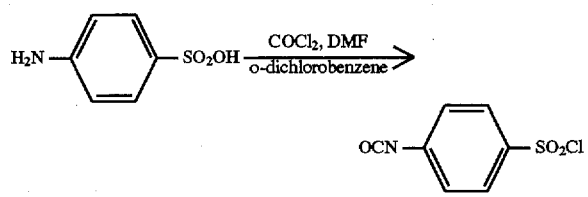

| Materials | mw | amount | mol | equiv |
|---|---|---|---|---|
| Sulfanilic acid | 173.2 | 1.84 kg | 10.6 | 1.00 |
| Phosgene | 98.9 | 2.23 kg | 22.5 | 1.06 |
| o-Dichlorobenzene | | 7.1 L | | |
| Dimethyl formamide | 73.10 | 92 g | 1.26 | 0.12 |
| Toluene (K.F. <100 µg/mL) | | 7 L | | |
| Isooctane | | 20 L | | |
| Product | | Theory | | |
| p-Chlorosulfonylisocyanate | 217.6 | 2.30 kg | 10.6 | 1.00 |

Procedure

A 22-L vessel was fitted with a gas inlet, thermocouple, dry ice condenser, mechanical stirrer, addition funnel (without pressure-equallization arm), and scrubber (the scrubber was washed with circulating 1M aqueous NaOH to decompose phosgene and neutralize HCl). To the vessel was charged sulfanilic acid (1.84 kg, 10.6 mol) and o-dichlorobenzene (6.4 L).

Caution: Proper safety measures must be taken during the operation?

The slurry was heated at ~165° C. and phosgene was passed into the vessel at a rate of ~7 g/min. Concurrently, a solution of dimethylformamide (92 g, 1.26 mol) in o-dichlorobenzene (700 mL) was added via the addition funnel over a period of 4 h. After the addition of DMF, the addition of phosgene was continued until a total of 2.23 kg was introduced while keeping the temperature at ~165° C.

The mixture was aged for 1 h at 165° C. after the addition of phosgene, then purged with nitrogen at 165° C. for 90 min. It was cooled to ~40° C. and diluted with dry toluene (6 L, K.F.<100 µg/mL) and filtered.

Caution: The mixture must be tested to ensure complete removal of phosgene before the filtration. The product (~1.6 kg) is not completely soluble in o-dichlorobenzene (~7 L) and toluene is needed to keep it in solution for removal of the starting material and side products by filtration.

The solid was washed with 1 L of dry toluene and combined with the filtrate. It was concentrated under reduced pressure at ~80° C. to remove the solvents. Isooctane (12 L) was added while maintaining the temperature at >80° C. The solution was transferred (filtered if necessary) into a 50-L vessel. The residue was extracted with 4 L of isooctane at ~80° C. The isooctane extracts are combined and assayed by GC.

Some gummy residue remains undissolved in hot isooctane. The product separates (oil) and crystallizes from isooctane upon cooling.

Assay yield: 1.60 kg, 69%.

Step 5. Cycloaddition

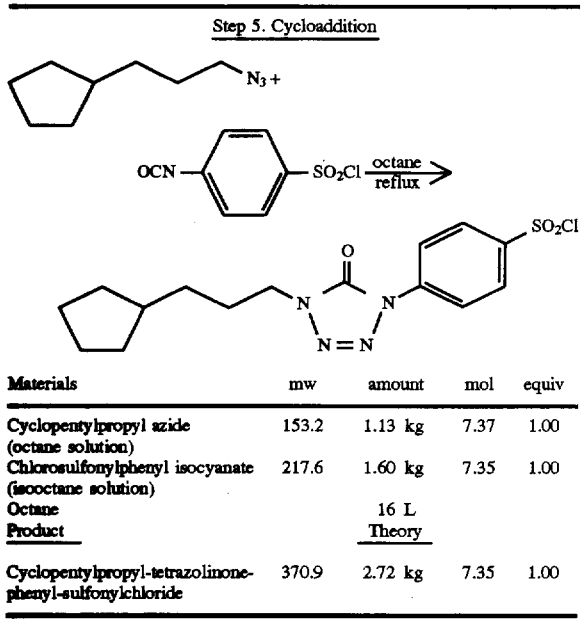

| Materials | mw | amount | mol | equiv |
|---|---|---|---|---|
| Cyclopentylpropyl azide (octane solution) | 153.2 | 1.13 kg | 7.37 | 1.00 |
| Chlorosulfonylphenyl isocyanate (isooctane solution) | 217.6 | 1.60 kg | 7.35 | 1.00 |
| Octane | | 16 L | | |
| Product | | Theory | | |
| Cyclopentylpropyl-tetrazolinone-phenyl-sulfonylchloride | 370.9 | 2.72 kg | 7.35 | 1.00 |

Procedure

The chlorosulfonylphenyl isocyanate/isooctane mixture in a 50-L vessel from step 4 was concentrated at ~60° C. under reduced pressure to a volume of ~4 L. The octane solution of cyclopentylpropyl azide (step 3, ~14 L, 1.13 kg, 7.37 mol of alkyl azide) was charged and the resulting solution was further distilled under nitrogen (~1 atm) until the batch temperature reached 125° C. The remaining solution (~14 L) was heated at reflux under nitrogen for 24 h. The reaction was assayed by NMR.

Caution: Heat may not be applied above the liquid level of the reaction mixture as splashing may occur and the potentially shock sensitive azide and the product may be concentrated on the side of the vessel.

Due to the potential thermal hazards of this reaction, great caution must be taken while running the reaction.

The reaction is 50–55% complete after 24 h.

The solution was then concentrated by distillation under nitrogen until ~5 L of distillate was collected (~9 L left in the reaction vessel). It was further refluxed for 24 h and the reaction was assayed by NMR.

The solution was then diluted with 8 L of dry n-octane (K.F.<100 μL/mL) at ~100° C. and the resulting solution was transferred (filtered if necessary) to a dry 22-L vessel. The solution was allowed to cool to 10°–15° C. over 2 h and aged for 1 h under nitrogen.

The mixture was filtered under nitrogen and the solid was washed with 2×4 L of dry octane. The solid was dried in vacuo (30° C., nitrogen sweep).

Yield: 1.72 kg, 63%.

The filtrate and wash were combined, concentrated to ~3 L, and further refluxed for 40 h. It was then diluted with 2 L of n-octane at ~120° C. and filtered. The filtrate was cooled to 10°–15° C., aged for 1 h, and filtered. The solid was washed with 2×300 mL of n-octane and dried in vacuo (30° C., nitrogen sweep).

Yield: 504 g, 18.5%.

Recrystallization of the first crop of product

To a 50-L vessel was charged 1.72 kg of the product and 32 L of dry heptane (K.F.<100 μg/mL). The mixture was heated under nitrogen to 95° C.

The solution was transferred while still hot through an in-line falter (10μ) using teflon tubing into a 50-L vessel. The gummy residue was extracted with 2 L of hot heptane. The solution was concentrated under reduced pressure at ~50° C. to ~16 L.

The slurry was heated under nitrogen until the solid dissolved (~80° C.). The solution was allowed to cool to 20° C. over 6 h. The mixture was further cooled at 0°–5° C. for 2 h then filtered. The cake was washed with 2×1.5 L of cold heptane and dried by suction under nitrogen for 1 h. The solid was further dried in vacuo (30° C., N₂ sweep) to constant weight.

Recovery yield: 1.60 kg, 93%.

What is claimed is:

1. A process for the preparation of a compound of structural formula 7:

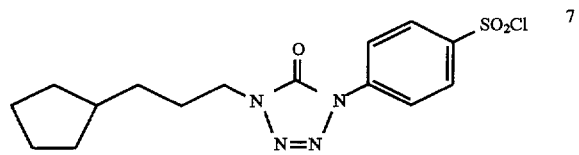

which comprises the steps of:

A. treating a compound of structural formula 2

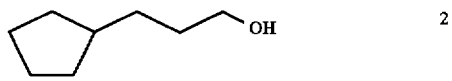

with a sulfonylating reagent selected from methanesulfonyl chloride, benzesulfonyl chloride or toluenesulfonyl chloride in toluene in the presence of a strong organic base at about −10° to −40° C. to yield the compound of structural formula 3:

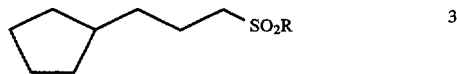

wherein R is —CH₃, phenyl or tolyl:

B. treating 3 with sodium azide in dimethyl sulfoxide at about 30°–60° C. to yield the compound of structural formula 4:

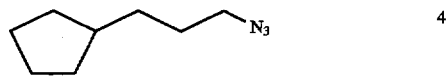

C. treating 4 with p-chlorsulfonylisocyanate of structural formula 6:

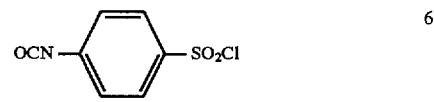

in an inert organic solvent to yield the product 7.

2. The process of claim 1 wherein the organic solvent of step C is n-octane.

3. The process of claim 1, wherein R is —CH₃.

4. The process of claim 2 wherein R is —CH₃.

5. The process of claim 1, Step B wherein the concentration of 3 is maintained below 130 g/L.

6. The process of claim 2 wherein the concentration of compound 3 in Step B is maintained below 130 g/L.

7. The process of claim 3, wherein the concentration of compound 3 in Step B is maintained below 130 g/L.

8. The process of claim 1, wherein the concentration of each reactant is 0.53M or less in Step C.

9. The process of claim 2, wherein the concentration of each reactant in Step C is 0.53M or less.

10. The process of claim 3, wherein the concentration of each reactant in Step C is 0.53M or less.

11. The process of claim 4, wherein the concentration of each reactant in Step C is 0.53M or less.

12. The process of claim 5, wherein the concentration of each reactant in Step C is 0.53M or less.

13. The process of claim 6, wherein the concentration of each reactant in Step C is 0.53M or less.

14. The process of claim 7 wherein the concentration of each reactant in Step C is 0.53M or less.

15. The process for the preparation of a compound of structural formula 7:

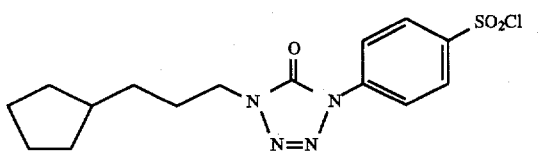

which comprises treating compound 4

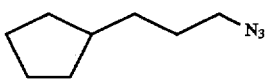

with p-chlorsulfonylisocyanate of structural formula 6:

in an inert organic solvent to yield the product 7.

16. The process of claim 15 wherein the reaction is conducted at 110°–150° C.

17. The process of claim 15 wherein the organic solvent is n-octane.

18. The process of claim 16, wherein the organic solvent is n-octane.

19. The process of claim 15 wherein the concentration of each reactant is 0.53M or less.

20. The process of claim 16 wherein the concentration of each reactant is 0.53M or less.

21. The process of claim 17 wherein the concentration of each reactant is 0.53M or less.

22. The process of claim 18 wherein the concentration of each reactant is 0.53M or less.

* * * * *